US009968417B2

(12) United States Patent
Johnson et al.

(10) Patent No.: US 9,968,417 B2
(45) Date of Patent: *May 15, 2018

(54) HANDS-FREE LIGHTING SYSTEM

(71) Applicant: Raptor Inventions, LLC, Burley, ID (US)

(72) Inventors: Neal Landon Johnson, Burley, ID (US); Stegen David Phillips, Burley, ID (US)

(73) Assignee: Raptor Inventions, LLC, Burley, ID (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/960,671

(22) Filed: Dec. 7, 2015

(65) Prior Publication Data

US 2016/0089215 A1    Mar. 31, 2016

Related U.S. Application Data

(63) Continuation of application No. 14/151,541, filed on Jan. 9, 2014, now Pat. No. 9,226,372.

(60) Provisional application No. 61/767,098, filed on Feb. 20, 2013, provisional application No. 61/750,436, filed on Jan. 9, 2013.

(51) Int. Cl.
| | |
|---|---|
| *A61C 1/08* | (2006.01) |
| *H05B 37/02* | (2006.01) |
| *H05B 33/08* | (2006.01) |
| *A61C 1/00* | (2006.01) |
| *A61C 13/15* | (2006.01) |
| *F21V 9/00* | (2018.01) |
| *F21V 23/00* | (2015.01) |
| *F21Y 115/10* | (2016.01) |

(52) U.S. Cl.
CPC ............ *A61C 1/088* (2013.01); *A61C 1/0015* (2013.01); *A61C 19/003* (2013.01); *F21V 9/00* (2013.01); *F21V 23/003* (2013.01); *F21V 23/008* (2013.01); *H05B 33/0857* (2013.01); *H05B 37/029* (2013.01); *H05B 37/0272* (2013.01); *F21Y 2115/10* (2016.08)

(58) Field of Classification Search
CPC ............ H05B 37/0245; H05B 33/0842; H05B 33/0839; H05B 33/0815; H05B 37/0263; H05B 37/0272; A61C 1/088; A61C 1/10; A61C 1/12; A61C 19/003; A61C 1/0015; F21V 23/003
USPC ..... 315/307, 308, 158, 312, 185 R; 362/105, 362/570–573, 804, 343, 319, 277
See application file for complete search history.

(56) References Cited

U.S. PATENT DOCUMENTS

| | | |
|---|---|---|
| 2,459,711 A | 1/1949 | Meier |
| 3,646,341 A | 2/1972 | Klatskin |
| 4,863,241 A | 9/1989 | Heun |
| 5,191,265 A | 3/1993 | D'Aleo et al. |

(Continued)

OTHER PUBLICATIONS

"Final Office Action", U.S. Appl. No. 14/151,541, May 18, 2015, 6 pages.

(Continued)

*Primary Examiner* — Haissa Philogene

(57) ABSTRACT

A hands-free lighting system comprising: a master control unit, a light unit, and a remote control unit. The master control unit is configured for controlling the operation of a remote light unit based on a signal received from a remote control unit. The light unit comprising at least one light source.

11 Claims, 13 Drawing Sheets

(56) References Cited

U.S. PATENT DOCUMENTS

| | | | |
|---|---|---|---|
| 5,430,620 | A | 7/1995 | Li et al. |
| 6,955,444 | B2 | 10/2005 | Gupta |
| 7,008,055 | B2 | 3/2006 | McLear et al. |
| 7,008,074 | B1 | 3/2006 | Halm |
| 7,114,823 | B2 * | 10/2006 | McCullough ....... F21V 33/0056 362/105 |
| 7,384,147 | B1 | 6/2008 | Ameri |
| 7,408,705 | B2 | 8/2008 | Horiguchi et al. |
| 7,431,453 | B2 | 10/2008 | Hogan |
| 8,021,148 | B2 | 9/2011 | Goodson et al. |
| 8,152,340 | B1 | 4/2012 | Nguyen |
| 8,282,227 | B2 | 10/2012 | Massara et al. |
| 8,337,036 | B2 | 12/2012 | Soto et al. |
| 8,350,497 | B2 * | 1/2013 | Peting ................ H05B 37/0245 315/169.3 |
| 8,405,489 | B1 | 3/2013 | Halm |
| 8,425,072 | B2 | 4/2013 | Hurwitz |
| 8,467,133 | B2 * | 6/2013 | Miller ................. G02B 27/017 353/28 |
| 8,476,565 | B2 * | 7/2013 | Verfuerth .......... H05B 37/0272 250/205 |
| 8,757,831 | B2 | 6/2014 | Waters |
| 8,772,691 | B2 * | 7/2014 | May ...................... G01J 3/0254 250/205 |
| 8,814,691 | B2 * | 8/2014 | Haddick ............. G02B 27/017 463/30 |
| 9,049,753 | B1 * | 6/2015 | Wassel ................... H05B 37/02 |
| 9,206,969 | B2 * | 12/2015 | Bushee ............... F21V 23/0414 |
| 9,226,372 | B2 * | 12/2015 | Johnson ............. H05B 33/0857 |
| 9,610,137 | B1 * | 4/2017 | Kris ....................... A61C 1/088 |
| 9,631,806 | B2 * | 4/2017 | Mabry ................ F21V 33/0064 |
| 2002/0013532 | A1 | 1/2002 | Czubko et al. |
| 2004/0052479 | A1 | 3/2004 | Lane |
| 2005/0090730 | A1 | 4/2005 | Cortinovis et al. |
| 2005/0099824 | A1 | 5/2005 | Dowling et al. |
| 2006/0285316 | A1 | 12/2006 | Tufenkjian et al. |
| 2007/0258248 | A1 | 11/2007 | Duhe |
| 2008/0192459 | A1 | 8/2008 | Kwok |
| 2008/0253109 | A1 | 10/2008 | Canino et al. |
| 2008/0310145 | A1 | 12/2008 | Blake et al. |
| 2011/0105851 | A1 | 5/2011 | Horvath |
| 2011/0199755 | A1 | 8/2011 | Falk et al. |
| 2011/0227509 | A1 | 9/2011 | Saleh |
| 2012/0228463 | A1 | 9/2012 | Nelson et al. |
| 2012/0275140 | A1 | 11/2012 | Feinbloom et al. |
| 2012/0327643 | A1 | 12/2012 | Nguyen |
| 2013/0111651 | A1 | 5/2013 | Waters |
| 2014/0191664 | A1 | 7/2014 | Johnson et al. |
| 2017/0367785 | A1 * | 12/2017 | Munari ................. A61C 1/088 |

OTHER PUBLICATIONS

"Non-Final Office Action", U.S. Appl. No. 14/151,541, Sep. 25, 2014, 5 pages.

"Notice of Allowance", U.S. Appl. No. 14/151,541, Aug. 28, 2015, 8 pages.

"Ultra Light Optics", retrieved from http://ultralightoptics.com/overview.html on Dec. 14, 2012, 2 pages.

* cited by examiner

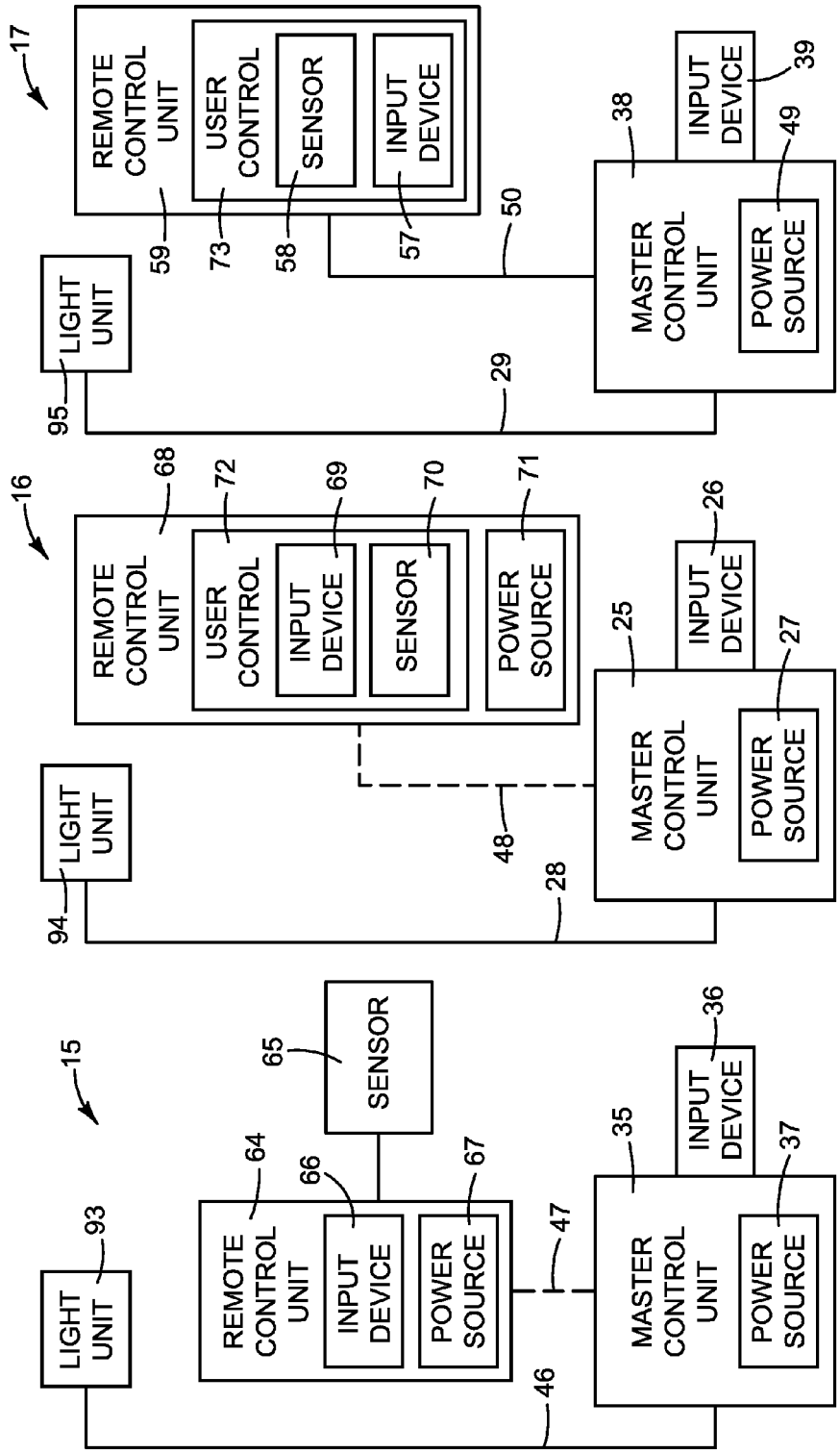

HANDS-FREE LIGHTING SYSTEM

PRIORITY/CROSS-REFERENCE TO RELATED APPLICATIONS

This application claims the benefit of U.S. Provisional Application No. 61/750,436, filed 9 Jan. 2013, the disclosure of which is incorporated by reference. This application also claims the benefit of U.S. Provisional Application No. 61/767,098, filed 20 Feb. 2013, the disclosure of which is incorporated by reference.

TECHNICAL FIELD

The disclosure generally relates to the field of lighting. Particular embodiments relate to dental lighting instruments.

BACKGROUND

Disclosed herein are hands-free lighting systems. Some exemplary hands-free lighting systems comprise a light unit, a master control unit and a remote control unit. Exemplary hands-free lighting systems could be particularly useful to a dentist in attending to the care of his/her patient.

SUMMARY OF THE DISCLOSURE

Several exemplary hands-free lighting systems are described herein.

Additional understanding of the devices and methods contemplated and/or claimed by the inventors can be gained by reviewing the detailed description of exemplary devices and methods, presented below, and the referenced drawings.

BRIEF DESCRIPTION OF THE DRAWINGS

FIG. 4 is a block diagram illustrating a sixth exemplary hands-free lighting system.

FIG. 5 is a block diagram illustrating a seventh exemplary hands-free lighting system.

FIG. 6 is a block diagram illustrating an eighth exemplary hands-free lighting system.

DETAILED DESCRIPTION

Figure 1A:
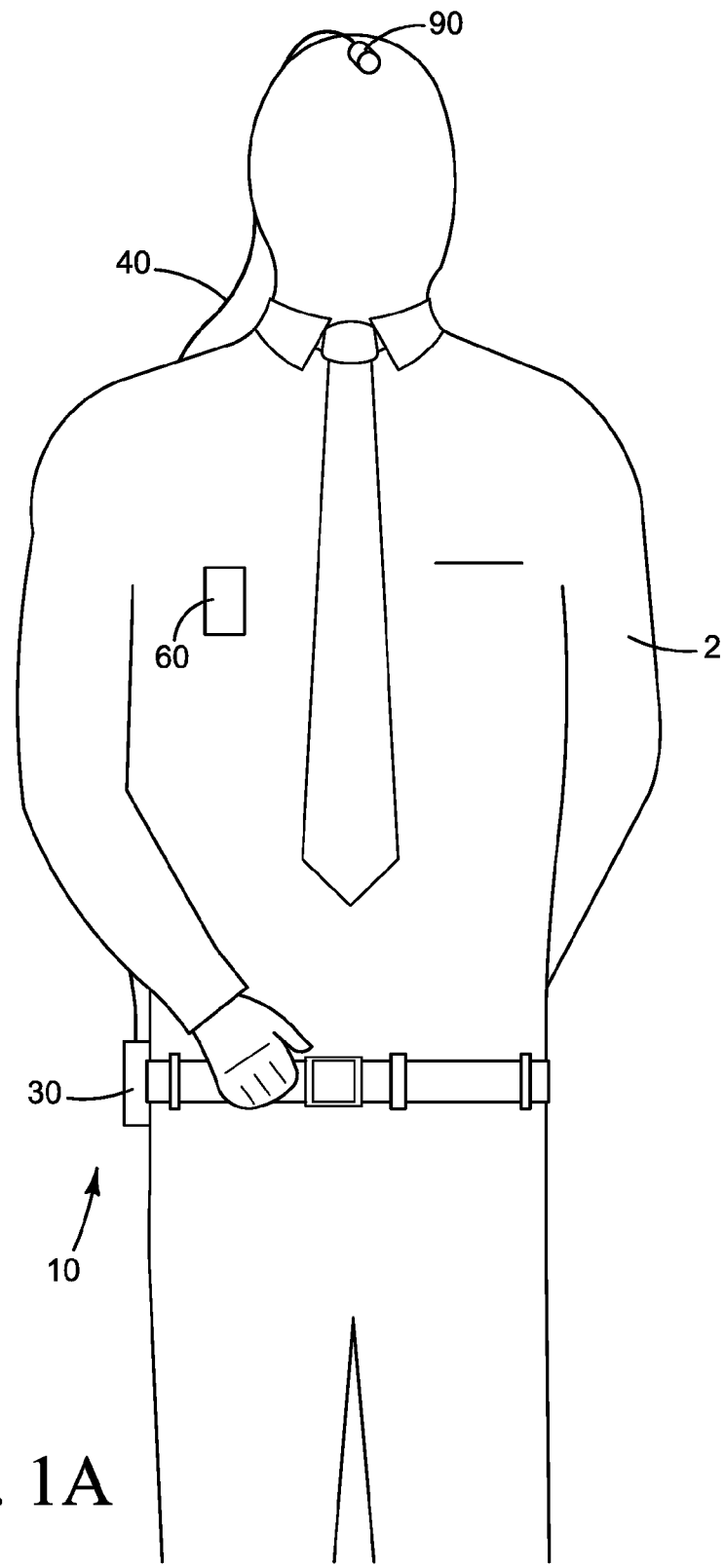
FIG. 1A is an environmental view of a user wearing a first exemplary hands-free lighting system, illustrating a master control unit worn on a user's belt, the master control unit connecting via a wire to a LED head light, and a remote control unit/sensor pinned on the user's chest.

The following description and the referenced drawings provide illustrative examples of that which the inventors regard as their invention. As such, the embodiments discussed herein are merely exemplary in nature and are not intended to limit the scope of the invention, or its protection, in any manner. Rather, the description and illustration of these embodiments serve to enable a person of ordinary skill in the relevant art to practice the invention.

The use of "e.g.," "etc," "for instance," "in example," "for example," and "or" and grammatically related terms indicates non-exclusive alternatives without limitation, unless otherwise noted. The use of "including" and grammatically related terms means "including, but not limited to," unless otherwise noted. The use of the articles "a," "an" and "the" are meant to be interpreted as referring to the singular as well as the plural, unless the context clearly dictates otherwise. Thus, for example, reference to "a sensor" includes two or more such sensors, and the like. The use of "optionally," "alternatively," and grammatically related terms means that the subsequently described element, event or circumstance may or may not be present/occur, and that the description includes instances where said element, event or circumstance occurs and instances where it does not. The use of "preferred," "preferably," and grammatically related terms means that a specified element or technique is more acceptable than another, but not that such specified element or technique is a necessity, unless the context clearly dictates otherwise. The use of "exemplary" means "an example of" and is not intended to convey a meaning of an ideal or preferred embodiment.

The use of "power source" means any device or mechanism by which electrical power may be supplied, such as batteries, power supplies, generators, capacitors, fuel cells, AC power sources, or any other type of electrical power supply, unless the context clearly dictates otherwise.

The use of "input device" means a component for allowing a user to provide input or otherwise control the operation of a connected device, including, but not limited to buttons, switches, keyboards, and cursor controls, unless the context clearly dictates otherwise.

The use of "sensor" means any device that performs a measurement of its environment and transmits a signal regarding that measurement, including but not limited to, capacitive sensors, proximity sensors, switches, buttons, sound/voice control sensors, RFID, infrared, accelerometers, and gyroscopes, unless the context clearly dictates otherwise.

The use of "proximity sensor" means a sensor able to detect the presence of nearby objects without any physical contact, unless the context clearly dictates otherwise.

The use of "user control" means an input device, sensor, or other system for allowing a user to control a component or system.

The use of "light source" means any light generating source, including, but not limited to, light emitting diodes, fluorescent lamps, incandescent lamps, and high-intensity discharge lamps, unless the context clearly dictates otherwise.

The use of "wireless connection" means any wireless signal, data, communication, or other interface including without limitation WiFi, Bluetooth, RF, acoustic, and infrared, unless the context clearly dictates otherwise.

The use of "connects" and "connected" includes direct wired connections, direct wireless connections, and connection via a network, such as a local area network (LAN), a wide area network (WAN) and/or the Internet, unless the context clearly dictates otherwise.

The use of "accelerometer" means any type of device, instrument or technique for obtaining measurements of proper acceleration, or acceleration of an inertial reference frame relative to itself, unless the context clearly dictates otherwise.

The use of "dental curing light" means a piece of dental equipment that is used for polymerization of light cure resin based composites, including, but are not limited to, composite resins, resin modified glass ionomers, resin cements, adhesive cements, and veneer cements, unless the context clearly dictates otherwise.

The use of "illuminating light" means a light that does not emit light in the visible blue light spectrum, unless the context clearly dictates otherwise.

Disclosed herein are a plurality of exemplary hands-free lighting systems comprising a light unit, a master control unit and a remote control unit, as well as lighting units. The hands-free lighting system particularly useful to a dentist in attending to the care of his/her patient.

FIG. 1A is an illustration of an environmental view of a user 2 wearing a first exemplary hands-free lighting system 10. The system 10 comprising a master control unit 30 which is preferably worn on a user's body, for instance on the user's waist belt. The master control unit 30 for controlling a connected light unit 90. In this exemplary system, the master control unit 30 connects via a wire 40 to the light unit 90, and supplies power to the light unit 90. In other exemplary systems, the master control unit may wirelessly connect (via a wireless connection) to the light unit and the light unit may be powered via an independent power source.

The system 10 further comprises a remote control unit 60 for controlling operation of the system 10. In this exemplary system 10, the remote control unit 60 connects wirelessly with the master control unit 30 and allows a user to control the operation of the light unit 90, e.g., turning the light unit 90 on and off, switching between and/or selecting light sources, increasing/decreasing brightness. As illustrated in this figure, the remote control unit 60 can be located adjacent the user's body, for instance pinned on the user's chest, or placed in a pocket of a garment worn by the user. Alternatively, the remote control unit could be placed on, or attached to, a work surface, or as otherwise needed for convenient access by the user.

Figure 1B:
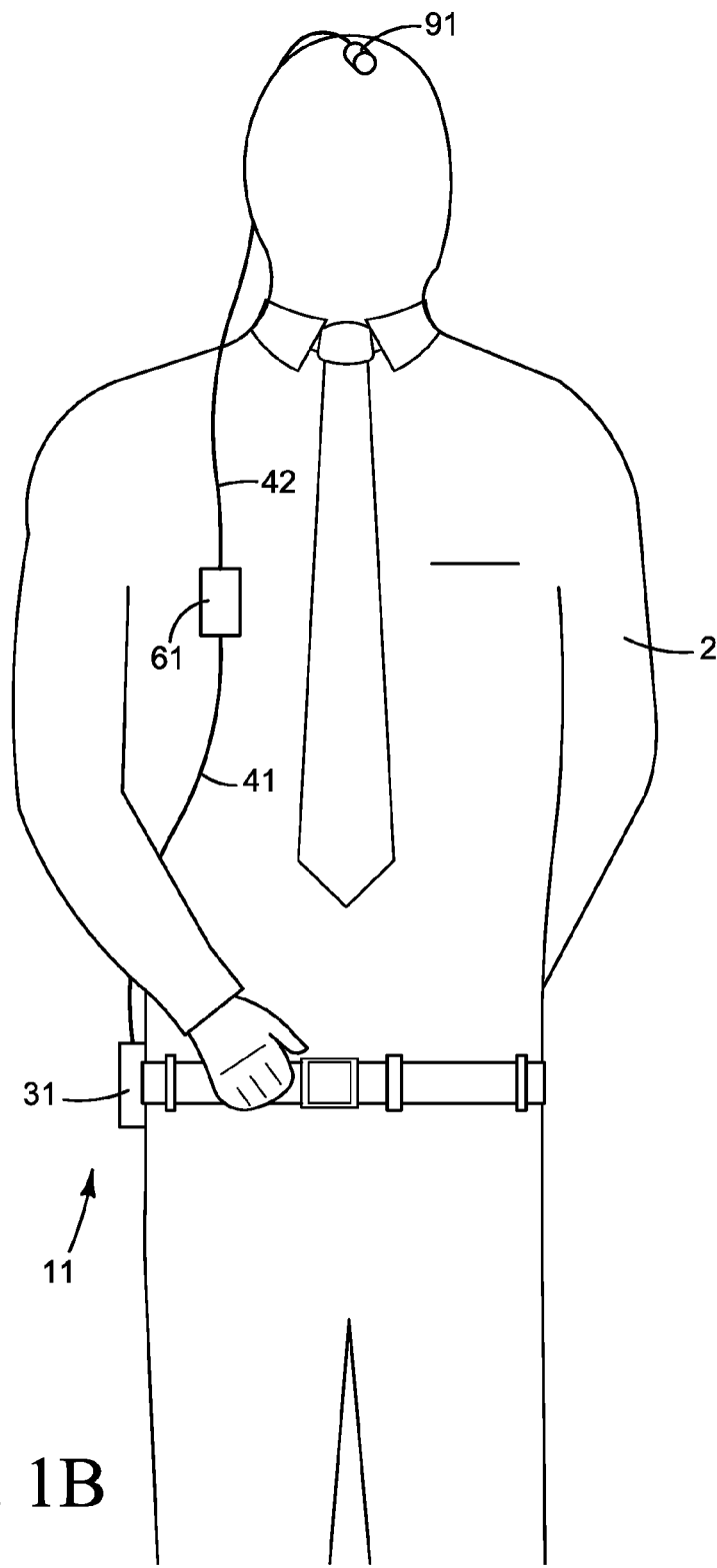
FIG. 1B is an environmental view of a user wearing a second exemplary hands-free lighting system, illustrating a master control unit worn on a user's belt, the master control unit connecting via a wire to a LED head light, with the remote control unit/sensor wired inline and pinned on the user's chest.

FIG. 1B is an environmental view of a user 2 wearing a second exemplary hands-free lighting system 11. The system 11 comprising a master control unit 31 which is preferably worn on a user's body, for instance on the user's waist belt. The master control unit 31 for controlling a connected light unit 91. In this exemplary system, the master control unit 31 connects via a wire 41 to a remote control unit 61 which connects via a wire 42 to the light unit 91. Alternatively, the master control unit 31 could be directly wired to the light unit 91. The master control unit 31 supplying power to the light unit 90. Alternatively, the remote control unit 61 could supply power to the light unit 91, or the light unit 91 may be powered via an independent power source. The remote control unit 61 for controlling operation of the system 11.

In this exemplary system 11, the remote control unit 61 connects via a wire 41 to the master control unit 31 and allows a user to control the light unit 91, e.g., turning the light unit 91 on and off, switching between and/or selecting light sources, increasing/decreasing brightness. As illustrated in this figure, the remote control unit 61 is located adjacent the user's body, for instance pinned on the user's chest, or placed in a pocket of a garment worn by the user. Alternatively, the remote control unit 61 could be placed anywhere along the source of power, e.g., in the cord, on or in the dental loupe frames, on or within headgear, on or within the housing of the light unit 91.

Figure 1C:
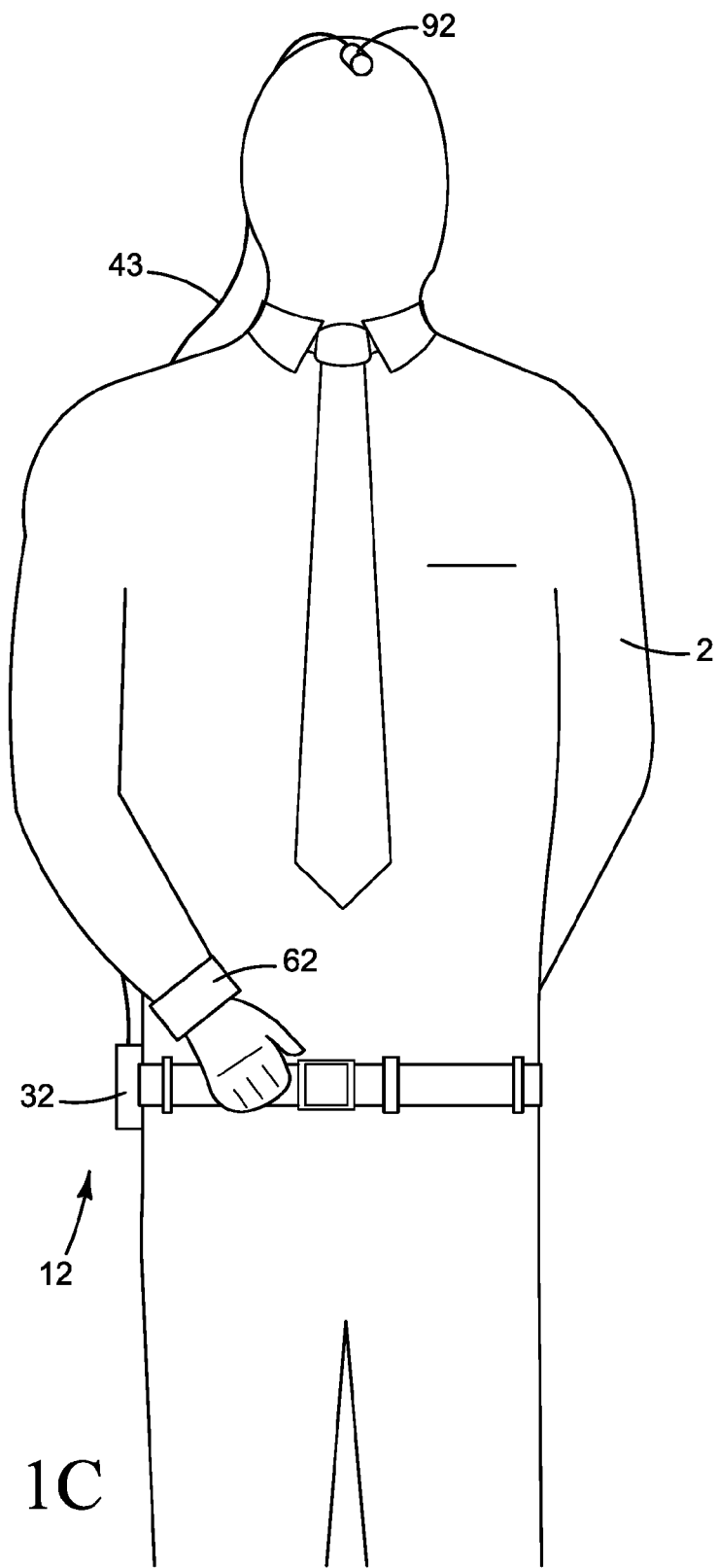
FIG. 1C is an environmental view of a user wearing a third exemplary hands-free lighting system, illustrating a master control unit worn on a user's belt, the master control unit connecting via a wire to a LED head light, and a remote control unit/sensor worn on a user's wrist.

FIG. 1C is an environmental view of a user 2 wearing a third exemplary hands-free lighting system 12. The system 12 comprising a master control unit 32 which is preferably worn on a user's body, for instance on the user's waist belt. The master control unit 32 for controlling a connected light unit 92. In this exemplary system, the master control unit 32 connects via a wire 43 to the light unit 92. The master control unit 32 supplying power to the light unit 92. Alternatively, the light unit 92 may be powered via an independent power source. The remote control unit 62 for controlling operation of the system 12. In this exemplary system 12, the remote control unit 62 connects wirelessly to the master control unit 32 via a wireless connection and allows a user to control the light unit 92, e.g., turning the light unit 92 on and off, switching between and/or selecting light sources, increasing/decreasing brightness. As illustrated in this figure, the remote control unit 62 is located adjacent the user's body, for instance worn as a bracelet on the user's wrist.

Figure 2:
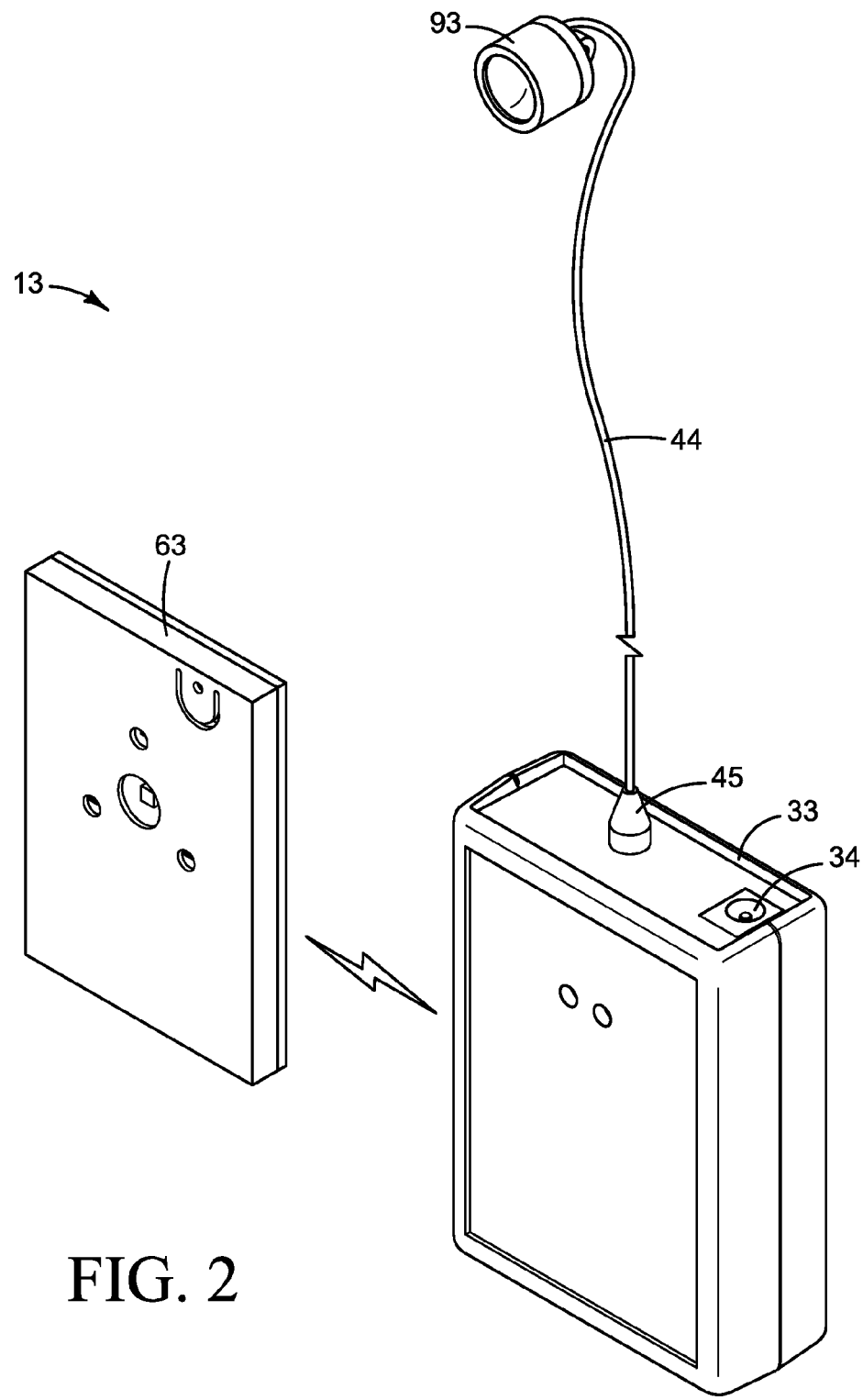
FIG. 2 is a perspective view of a fourth exemplary hands-free lighting system.

FIG. 2 is a perspective view of a fourth exemplary hands-free lighting system 13. The system 13 comprising a master control unit 33 which is preferably worn on a user's body, for instance on the user's waist belt or in the pocket of a garment worn by the user. The master control unit 33 for controlling a connected light unit 93. In this exemplary system 13, the master control unit 33 connects via a wired connection 44 to the light unit 93. The wired connection 44 terminating in a plug 45 which electrically connects with a receptacle 151 (illustrated in FIG. 13) on the master control unit 33. The receptacle 151 can be a 3.5 mm headphone plug jack, or other suitable electrical connection.

The master control unit 33 preferably containing a power source for powering the master control unit 33. In the fourth exemplary hands-free lighting system 13, the power source comprises a rechargeable battery 155 (illustrated in FIG. 13) located in the master control unit 33, the rechargeable battery 155 for supplying power to the light unit 93 via the wired connection 44. The rechargeable battery 155 could be rechargeable through connecting with a power transformer (not illustrated) plugged into power jack 34.

The remote control unit 63 for controlling operation of the fourth exemplary hands-free lighting system 13 based upon input received from a user. In the fourth exemplary hands-free lighting system 13, the remote control unit 63 connects wirelessly to the master control unit 33 via a wireless connection and allows a user to control the light unit 93 (e.g., turning the light unit 93 on and off, switching between and/or selecting light sources, increasing/decreasing brightness) via a user control portion.

Figure 3:
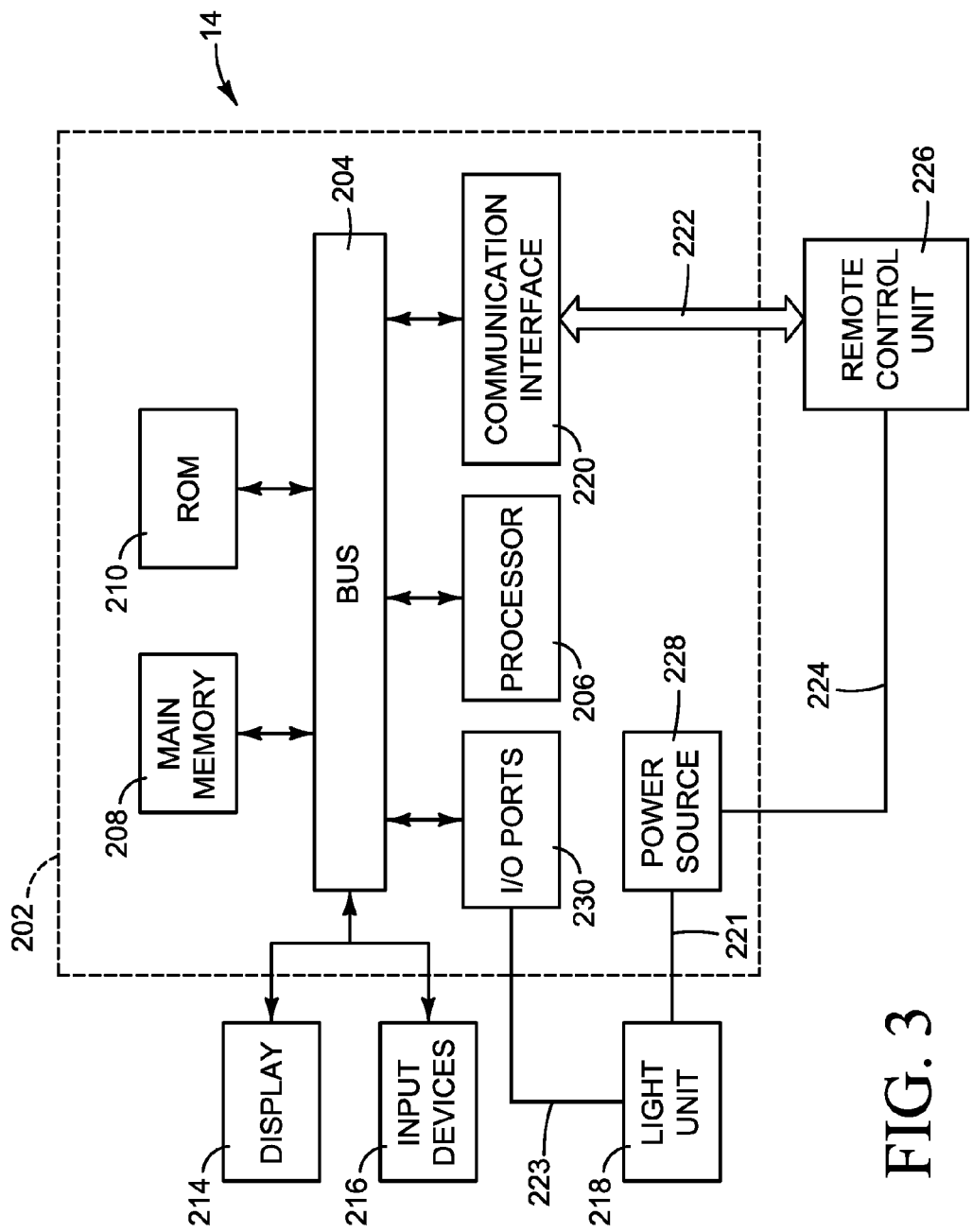
FIG. 3 is a block diagram illustrating a fifth exemplary hands-free lighting system.
Figure 7:
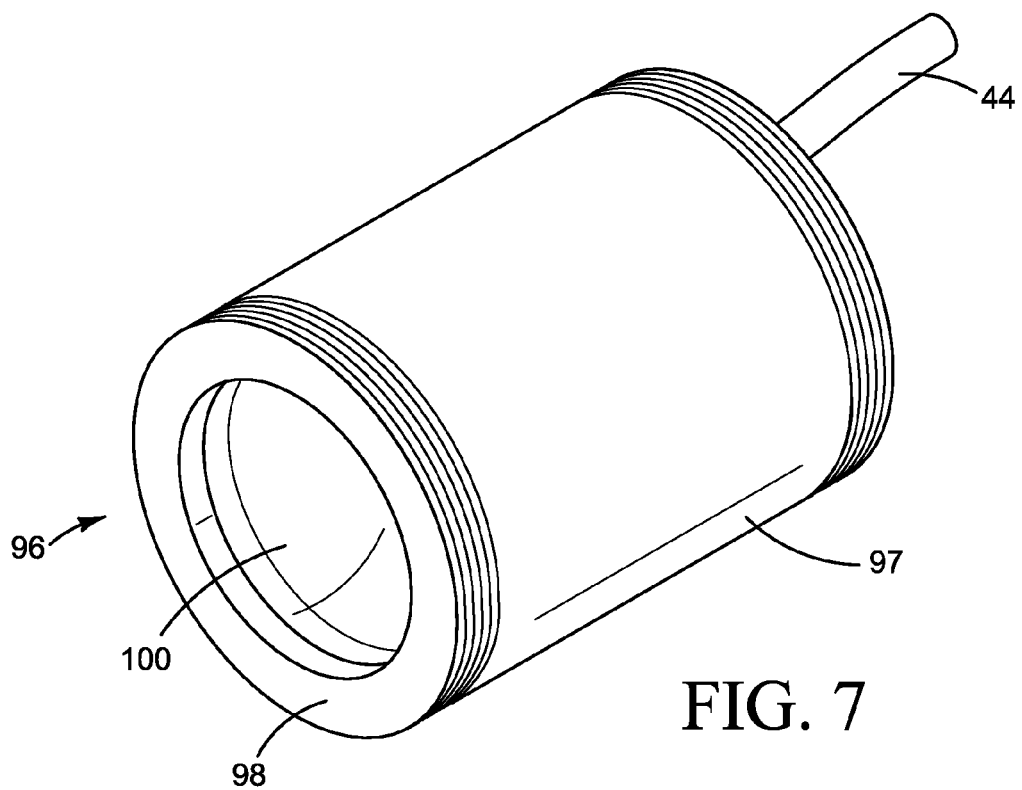
FIG. 7 is a front perspective view illustrating a first exemplary lighting unit.
Figure 8:
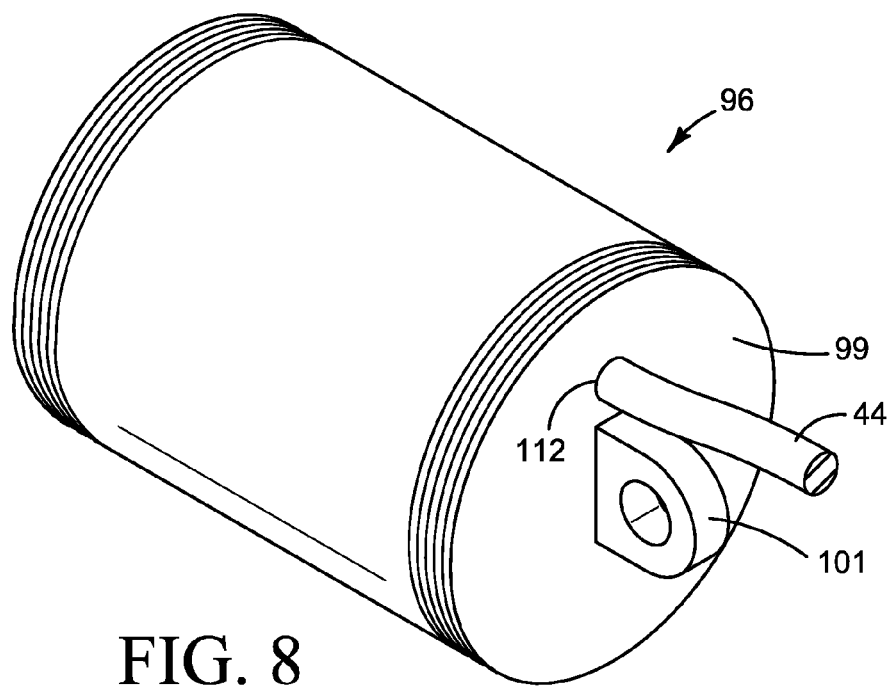
FIG. 8 is a rear perspective view of the lighting unit of FIG. 7.
Figure 9:
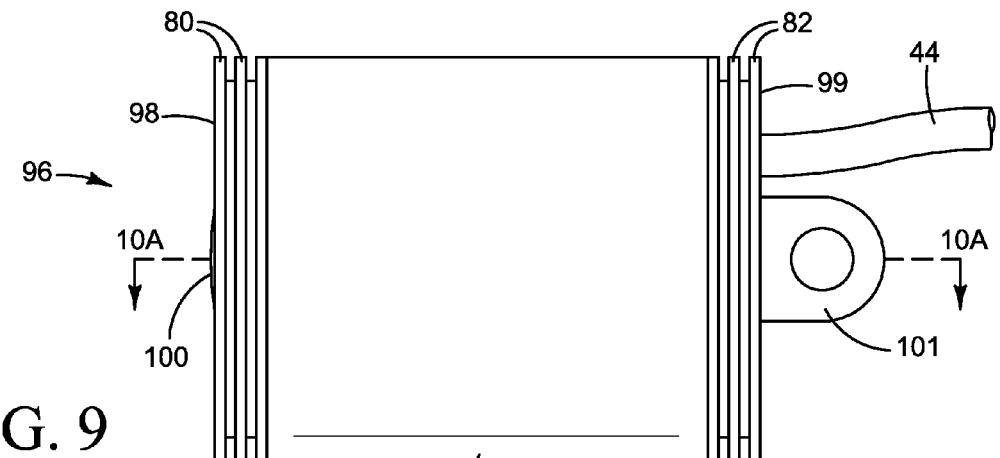
FIG. 9 is a side view of the lighting unit of FIG. 7.

FIG. 3 is a block diagram illustrating a fifth exemplary hands-free lighting system 14. FIG. 3 illustrates a master control system 202. Examples of exemplary master control systems 202 include, but are not limited to: a personal computer system, a work station computer system, a laptop computer system, a tablet computer system, an embedded controller system, a microprocessor-based system, a digital signal processor-based system, a handheld device system, a personal digital assistant (PDA) system, a wireless system, and a wireless networking system.

The master control system 202 includes a bus 204 or other communication mechanism for communicating information, and a processor 206 coupled with bus 204 for processing the information. The master control system 202 also includes a main memory 208, such as a random access memory (RAM) or other dynamic storage device (e.g., dynamic RAM (DRAM), static RAM (SRAM), synchronous DRAM (SDRAM), flash RAM), coupled to bus 204 for storing information and instructions to be executed by processor 206. In addition, main memory 208 may be used for storing temporary variables or other intermediate information during execution of instructions to be executed by processor 206. Master control system 202 may further include a read only memory (ROM) 210 or other static storage device (e.g., programmable ROM (PROM), erasable PROM (EPROM), and electrically erasable PROM (EEPROM)) coupled to bus 204 for storing static information and instructions for processor 206.

The master control system 202 also includes input/output ports 230 to couple the master control system 202 to external devices (e.g., the light unit 218), for implementing automatic control functions, remote control functions, etc. Such coupling may include, in example, direct electrical connections, wireless connections, networked connections, etc. The input/output ports 230 for allowing the master control system 202 to control the operation of the light unit 218 (e.g., turning the light unit 218 on/off, changing light sources, increasing/decreasing brightness), for instance via control connection 223.

The master control system 202 may comprise at least one power source 228. The power source 228 including, but not limited to one or more of: a rechargeable battery, a battery, an ultracapacitor, a power pack, and a connection with an external power source. The power source 228 for powering the master control system 202. Alternatively, the power source 228 could power the light unit 218 through a power connection 221. Alternatively, the power source 228 could power the remote control unit 226 through a power connection 224.

The master control system 202 may be coupled via bus 204 to a display 214 (e.g., liquid crystal display (LCD), light emitting diode (LED) display, voice synthesis hardware, voice synthesis software) for displaying and/or providing information to a user. The display 214 may be controlled by a display or graphics card.

The master control system 202 may include one or more input devices 216, including, but not limited to buttons, switches, keyboards, and cursor controls, for communicating information and command selections to processor 206. Alternatively, such command selections could be implemented via voice recognition hardware and/or software functioning as the input devices 216. A cursor control, for example, can comprise a mouse, a trackball, cursor direction keys, a touch screen display, optical character recognition hardware and/or software, etc. The cursor control for communicating direction information and command selections to processor 206 and for controlling cursor movement on the display 214.

The master control system 202 performs a portion or all of the processing steps of the hands-free lighting system in response to processor 206 executing one or more sequences of one or more instructions contained in a memory, such as the main memory 208. Such instructions may be read into the main memory 208 from another computer readable medium, such as a storage device. One or more processors in a multi-processing arrangement may also be employed to execute the sequences of instructions contained in main memory 208. In alternative embodiments, hard-wired circuitry may be used in place of or in combination with software instructions. Thus, embodiments are not limited to any specific combination of hardware circuitry and software.

As stated above, the master control system 202 includes at least one computer readable medium or memory programmed according to the teachings of hands-free lighting system and for containing data structures, tables, records, or other data described herein. Examples of computer readable media include, but are not limited to, PROMs (EPROM, EEPROM, flash EPROM), DRAM, SRAM, and SDRAM. Stored on any one or on a combination of computer readable media, the system includes software for controlling the master control system 202, for driving a device or devices for implementing the hands-free lighting system, and for enabling the master control system 202 to interact with a human user. Such software may include, but is not limited to, device drivers, operating systems, development tools, and applications software. Such computer readable media further includes the computer program product of the hands-free lighting system for performing all or a portion (if processing is distributed) of the processing performed in implementing the hands-free lighting system.

The master control system 202 also includes a communication interface 220 coupled to bus 204. Communication interface 220 provides a data communication coupling 222 for connection with a remote control unit 226. For example, communication interface 220 may be a network interface card used to attach to any packet switched local area network (LAN) to a remote control unit 226 via the data communication interface 220. As another example, the data communication interface 220 may comprise a radio frequency transceiver that establishes a wireless connection, wireless link, an RF link (e.g., a Bluetooth connection), or an infrared (IR) transceiver that establishes an IR link to the remote control unit 226. In another example, the communication coupling 222 may comprise a wired connection. In any such implementation, communication interface 220 sends and receives electrical, electromagnetic or optical signals that carry digital data streams representing various types of information to the remote control unit 226.

In preferred embodiments, communication coupling 222 preferably uses electrical, electromagnetic, or optical signals that carry digital data streams. The signals through the various networks and the signals through the communication coupling 222, and through communication interface 220, which carry the digital data to and from master control system 202, are exemplary forms of carrier waves transporting the information. The master control system 202 can transmit notifications and receive data, including program code, through the network(s), communication coupling 222 and communication interface 220.

FIG. 4 is a block diagram illustrating a sixth exemplary hands-free lighting system 15. The system 15 comprising a master control unit 35, a remote control unit 64 and a light unit 93. The master control unit 35 for controlling the operation of the light unit 93. The master control unit 35 comprising at least one input device 36 for allowing a user to operate the master control unit 35. The master control unit 35 including, or connecting to, a power source 37, such as a rechargeable battery. The power source 37 for powering the light unit 93 through the wired connection 46. The master control unit 35 preferably controlling the light unit 93 via a control signal sent through the wired connection 46. The light unit 93 comprising one or more light sources, such as light emitting diodes. The master control unit 35 wirelessly connects to the remote control unit 64 via a wireless connection 47.

The remote control unit 64 comprising at least one user control portion, such as an input device 66 and/or a sensor 65, for receiving at least one input from a user. The user control portion(s) for allowing a user to manually operate the remote control unit 64 or otherwise provide an input to the remote control unit 64. Alternatively, or in addition thereto, the remote control unit 64 could comprise at least one sensor 65 for sensing an input from the user. The sensor 65 preferably located external to the remote control unit 64. Wherein in response to user input, the remote control unit 64 sends a signal to the master control unit 35. The master control unit 35, upon receiving the signal from the remote control unit, then controls the light unit 93 as instructed by the signal (e.g., turning the light unit 93 on/off, changing light sources, increasing/decreasing brightness, interrupting power supplied to the light unit). The remote control unit 64 preferably comprises a power source 67, such as a rechargeable battery.

FIG. 5 is a block diagram illustrating a seventh exemplary hands-free lighting system 16. The system 16 comprising a master control unit 25, a remote control unit 68 and a light unit 94. The master control unit 25 for controlling the operation of the light unit 94. The master control unit 25 comprising at least one input device 26 for allowing a user to manually operate the master control unit 25. The master control unit 25 including, or connecting to, a power source 27, such as a rechargeable battery. The power source 27 for powering the light unit 94 through wired connection 28. The master control unit 25 preferably controlling the light unit 94 via a control signal sent through the wired connection 28. The light unit 94 comprising one or more light sources, such as light emitting diodes. The master control unit 25 wirelessly connects to the remote control unit 68 via a wireless connection 48.

The remote control unit 68 preferably comprising at least one input device 69 for allowing a user to operate the remote control unit 68. The remote control unit 68 comprising a power source 71, such as a rechargeable battery. The remote control unit 68 comprising a user control portion 72, such as an input device 69 and/or a sensor 70, for receiving at least one input from the user. If present, the input device(s) 69 is configured for allowing a user to manually operate the remote control unit 68 or otherwise provide an input to the remote control unit 68. If present, the sensor 70 is preferably located within the remote control unit 68, but could be separate therefrom. The sensor 70 for sensing an input from the user. The sensor 70 preferably located external to the remote control unit 68. Wherein in response to user input, the remote control unit 68 sends a signal to the master control unit 25. The master control unit 25, upon receiving the signal from the remote control unit, then controls the light unit 94 as instructed by the signal (e.g., turning the light unit 94 on/off, changing light sources, increasing/decreasing brightness, interrupting power supplied to the light unit). The remote control unit 68 preferably comprises a power source 71, such as a rechargeable battery.

FIG. 6 is a block diagram illustrating an eighth exemplary hands-free lighting system 17. The system 17 comprising a master control unit 38, a remote control unit 59 and a light unit 95. The master control unit 38 for controlling the operation of the light unit 95. The master control unit 38 comprising at least one input device 39 for allowing a user to manually operate the master control unit 38. The master control unit 38 including, or connecting to, a power source 49, such as a rechargeable battery. The power source 49 for powering the light unit 95 through wired connection 29, as well as the remote control unit 59 through wired connection 50. The master control unit 38 preferably controlling the light unit 95 via a control signal sent through the wired connection 29. The light unit 95 comprising one or more light sources, such as light emitting diodes. The master control unit 38 connects to the remote control unit 59 via a wired connection 50.

The remote control unit 59 preferably comprising a user control portion 73 for allowing a user to operate the remote control unit 59. The remote control unit 59 could comprise at least one input device and/or at least one sensor for receiving at least one input from a user. If present, the input device 57 for allowing a user to manually operate the remote control unit 59, or otherwise provide an input to the remote control unit 64. If present, the sensor 58 is configured for sensing an input from the user. The sensor 58 is preferably located within the remote control unit 59, but could be located remote thereto. Wherein in response to user input, the remote control unit 59 sends a signal to the master control unit 38. The master control unit 38, upon receiving the signal from the remote control unit, then controls the light unit 95 as instructed by the signal (e.g., turning the light unit 95 on/off, changing light sources, increasing/decreasing brightness, interrupting power supplied to the light unit).

FIGS. 7 through 9, 10A and 11 illustrate a first exemplary light unit 96. The first exemplary light unit 96 comprises a housing 97, a head cap 98, a tail cap 99, and at least one lens 100 located in the head cap 98. The lens 100 may comprise any necessary optics for enabling light emitted from the light unit 96 to be directed to a tight spot beam or as otherwise desired. The configuration disclosed with respect to the first exemplary light unit 96 is merely representative, and a skilled artisan will be able to select an appropriate structure and configuration in a particular embodiment based on various considerations, including the intended use of the light unit, the intended arena within which the light unit will be used, and the equipment and/or accessories with which the light unit is intended to be used, among other considerations. For instance, an exemplary light unit may or may not have such a housing configuration, and/or may not have a lens.

It is preferred that a connector be provided for enabling the light unit 96 to be mounted to a surface or an accessory, for instance the frame of a dentist's light loupe. The connector 101 illustrated in FIGS. 8, 9 and 10A comprising a male hinge connector extending from the tail cap 99 of the light unit 96. The connector 101 configured for receipt into a female, forked hinge connector (not illustrated), and rotationally connected thereto via a pin or other such connector. A skilled artisan will be able to select an appropriate type of connector, or manner of connecting the light unit to a surface or accessory, in a particular embodiment based on various considerations, including the intended use of the light unit or accessory, among other considerations.

Referring back to the first exemplary light unit 96, at least one light source 110 is located within, upon or connecting to the housing 97. As such, an exemplary light unit may comprise a plurality of light sources, each having or more light elements. In the embodiment illustrated in these figures, light source 110 comprises a first light element 120 and a second light element 130. One example of a suitable light element is a light emitting diode. Such light elements can be mounted on printed circuit boards, and can further comprise one or more heat sinks 80, 82 for the dissipation of heat, if necessary.

In the first exemplary light unit 96, a wired connection 44 is utilized to connect, at an electrical connection 112, the light source 110 to a power source, such as a battery. Alternatively, the light unit could comprise a power source for supplying power to the light element(s).

Figure 12:
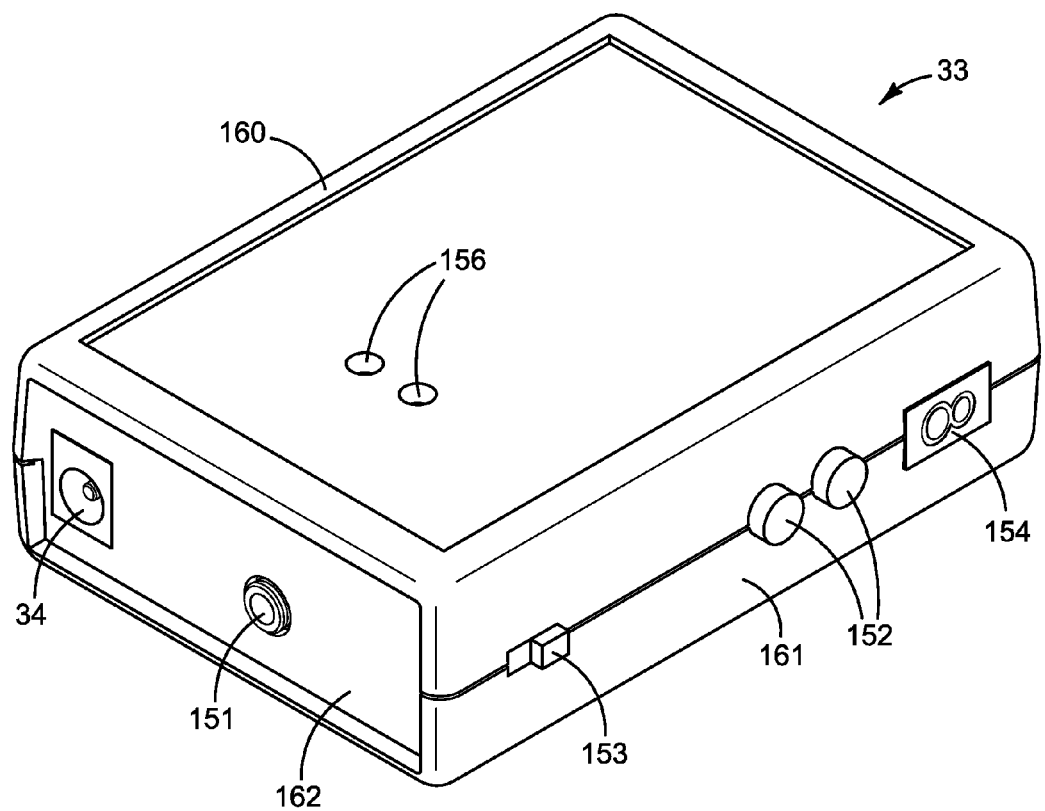
FIG. 12 is a perspective view of the master control unit of the fourth exemplary hands-free lighting system illustrated in FIG. 2.

The wired connection 44 can further comprise wiring for connecting the light source 110 to a controller, such as the master control unit 33 illustrated in FIG. 12. The master control unit 33 configured for controlling the operation of the light unit 96, e.g., turning the light unit 96 on and off, switching between and/or selecting light sources, increasing/decreasing the brightness/intensity of the light sources. Such control can be accomplished via a control signal sent by the master control unit 33, through the wired connection 44, and to the light unit 96.

Figure 10A:
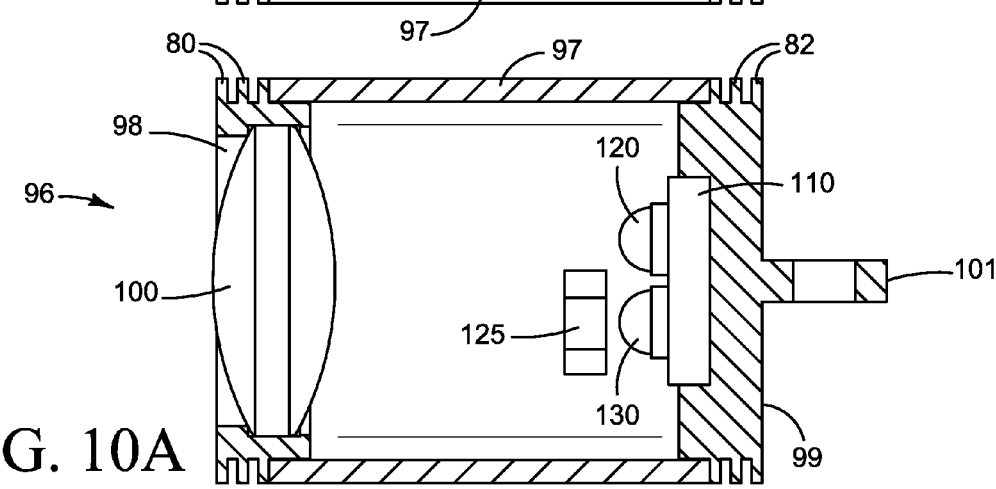
FIG. 10A is a cross-sectional view of the lighting unit of FIG. 7, along the lines 10A-10A of FIG. 9.
Figure 10B:
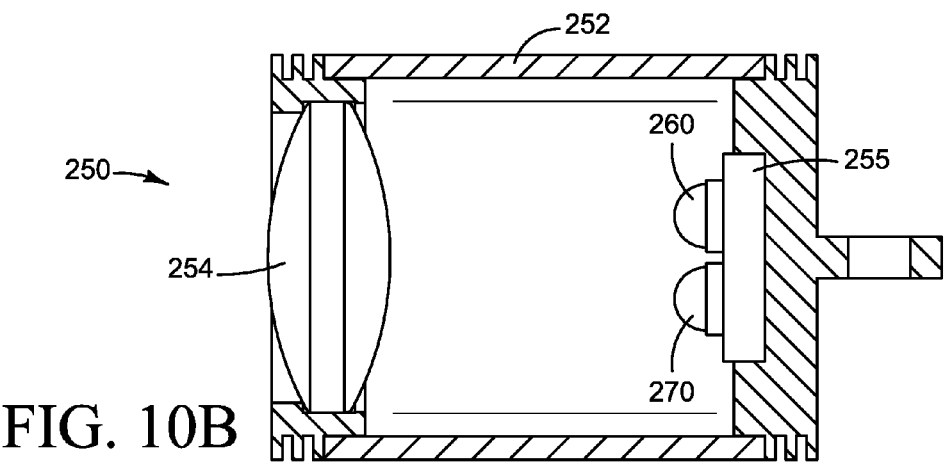
FIG. 10B is a cross-sectional view of a second exemplary lighting unit.
Figure 11:
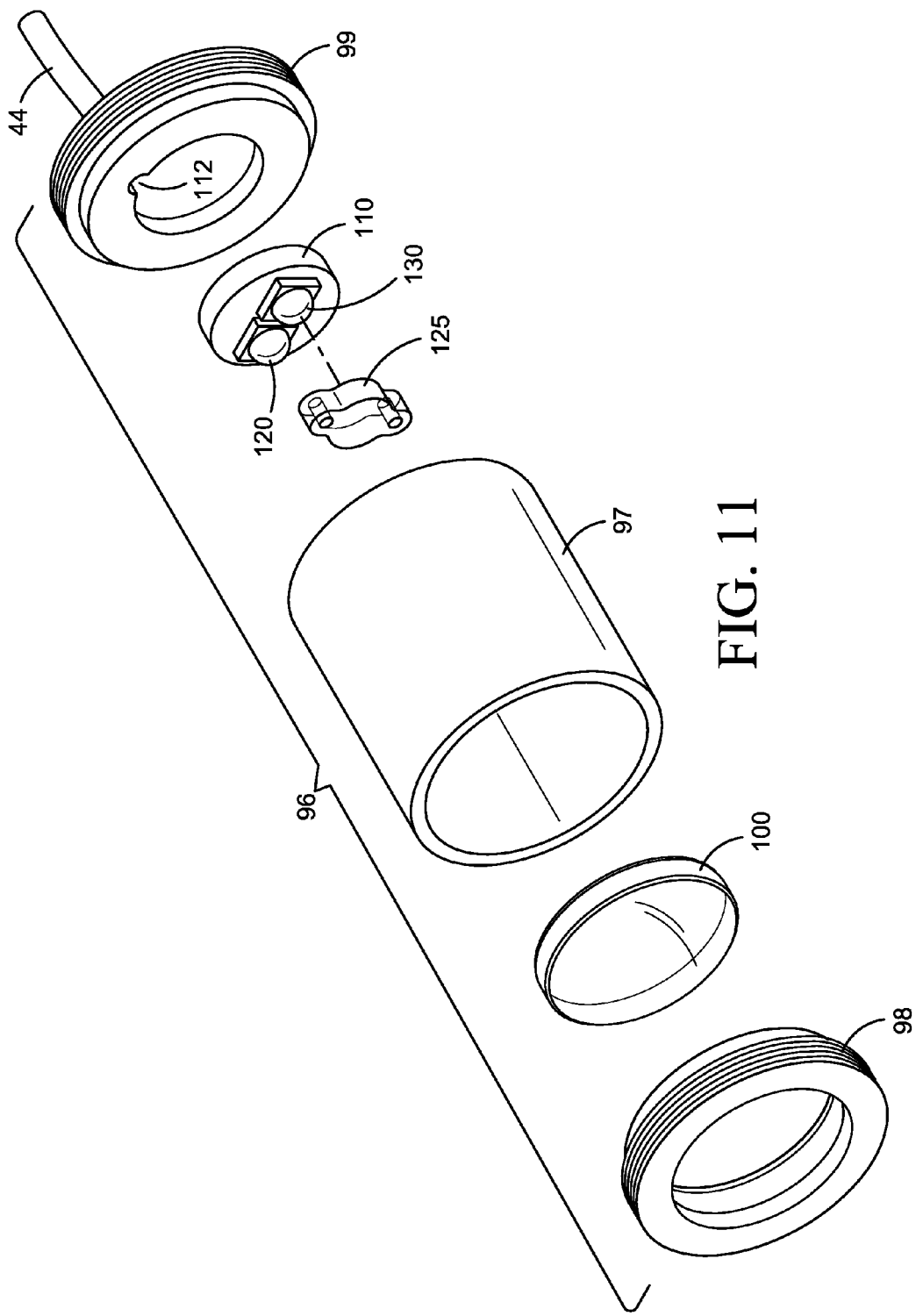
FIG. 11 is an exploded, perspective view of the lighting unit of FIG. 7.

The first exemplary light unit 96, as particularly illustrated in FIG. 10A, and the second exemplary light unit 250, as particularly illustrated in FIG. 10B, both comprise a dual-mode dental loupe light. The first exemplary light unit 96 comprises a curing light (the first light element 120) and an illuminating light (the second light element 130). Likewise, the second exemplary light unit 250 comprises a curing light (the first light element 260) and an illuminating light (the second light element 270). It is preferred that light emanating from the light unit which is generated by the first light element be different than the emanated light which is generated by the second light element.

Referring first to the first exemplary light unit 96 of FIG. 10A, the first exemplary light unit 96 further comprises a visible blue light spectrum filter 125 for preventing the passing of visible blue light through the filter 125, such as by filtering the wavelengths of 430 nanometers to 480 nanometers, or another such range or ranges. In such a configuration, the unfiltered light element 120 is configured as a dental curing light, whereas the filtered light element 130 can be illuminated without causing the curing of light sensitive dental materials. In such an exemplary light unit, the two light elements themselves could be identical to one another—both providing a spectrum of light including emitting light in the visible blue light spectrum. A skilled artisan will be able to select an appropriate structure and material for the filter in a particular embodiment based on various considerations, including the intended use of the system, among other considerations.

Referring now to the second exemplary light unit 250 of FIG. 10B, the first light element 260 provides a first wavelength range of light which does not include visible blue light, and the second light element 270 is configured as a dental curing light, emitting light in the visible blue light spectrum. For instance, the second light element 270 could comprise a light emitting diode emitting light in the visible blue light spectrum, such as a light emitting diode using gallium nitride as a semiconductor, whereas the first light element 260 could comprise a light emitting diode specifically configured for not producing light in the visible blue light spectrum. Unlike the exemplary light unit of FIG. 10A, no separate filter element is utilized.

A skilled artisan will be able to select an appropriate structure and material for such a configuration in a particular embodiment based on various considerations and methods, including but not limited to utilizing different types of light elements, and utilizing one or more filters on one, some or all of the light sources and/or elements.

The hands-free lighting systems disclosed above could be utilized with the exemplary light units disclosed above. For instance, light unit 96 could be incorporated into a dental light loupe worn by a dentist utilizing the seventh exemplary hand-free lighting system 16. Wherein the dentist, making hand gestures detected by the sensor 70 (and/or providing input via input device 69), could turn the curing light 120 on to polymerize light cure resign based composites, and then, via additional hand gestures or input, turn the curing light 120 off.

Figure 13:
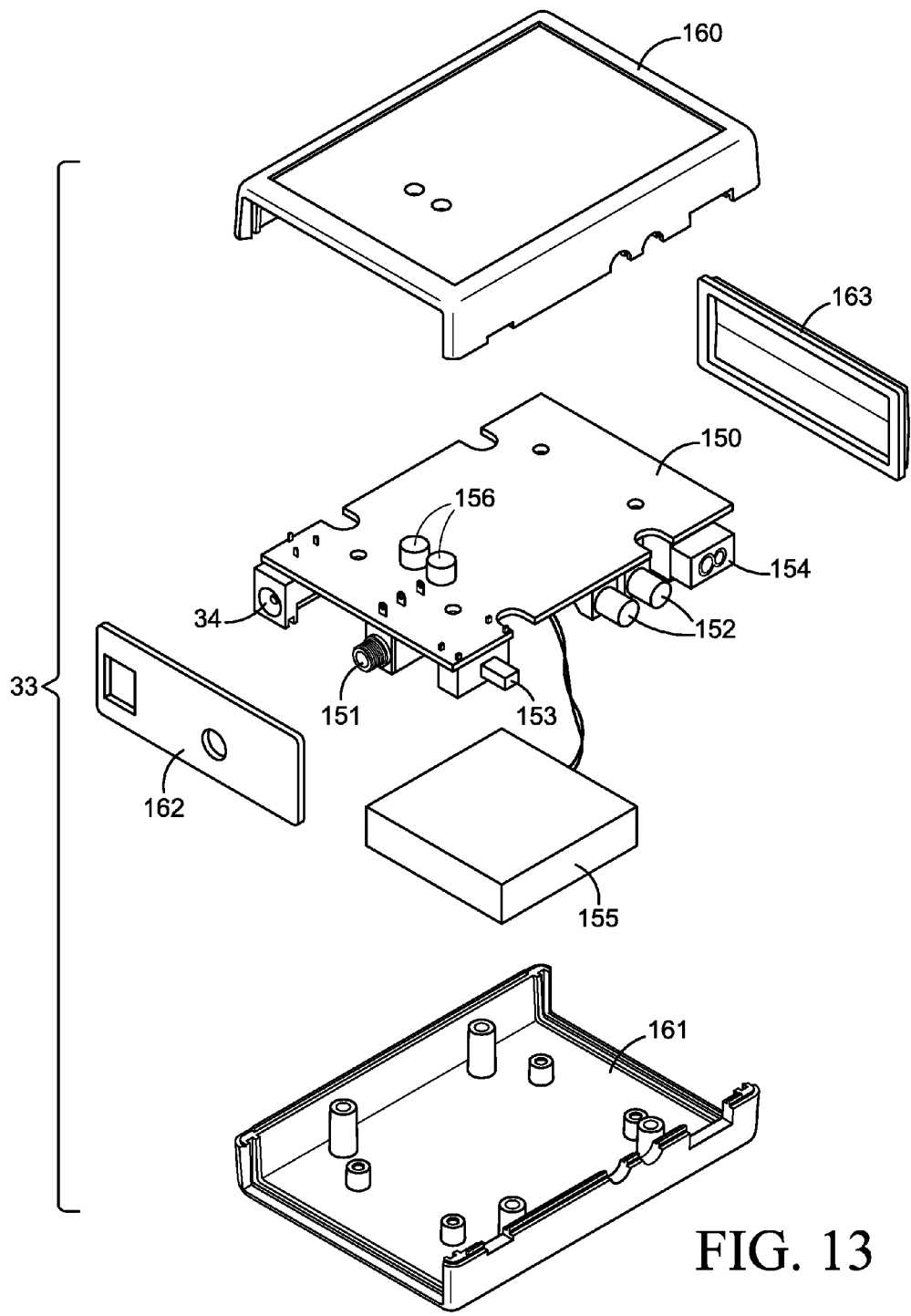
FIG. 13 is an exploded view of the master control unit of FIG. 12.

FIGS. 12 and 13 further illustrate the master control unit 33 of the fourth exemplary hands-free lighting system 13 illustrated in FIG. 2. The master control unit 33 for operating the light unit 93 (e.g., turning it on and off).

The master control unit 33 comprising a housing. The housing comprising a top case 160, a bottom case 161, a first end 162, and a second end 163. Other exemplary housings will be differently configured. A skilled artisan will be able to select an appropriate structure and configuration in a particular embodiment based on various considerations, including the intended use of the housing, the intended arena within which the housing will be used, and the equipment and/or accessories with which the housing is intended to contain, among other considerations.

Within the housing are located a printed circuit board 150 and a power source (e.g., a rechargeable battery 155). The printed circuit board 150 containing the electrical components necessary to operate the master control unit 33, such as described herein, including regarding the master control system 202.

The printed circuit board 150 further comprising a receptacle 151 or other electrical connection for connecting with the plug 45 of the wired connection 44 for the light unit 93, thereby enabling the master control unit 33, via the wired connection 44, to supply power (from the rechargeable battery 155) to the light unit 93. A skilled artisan will be able to select an appropriate structure and configuration for the receptacle and plug in a particular embodiment based on various considerations, including the intended use of the system, the intended arena within which the system will be used, and the equipment and/or accessories with which the system is intended to be used, among other considerations.

The printed circuit board 150 further comprising at least one input device for enabling a user to operate the master control unit 33. These input devices for enabling the operation of the system 13 to be manually controlled, without use of the remote control unit 63. Input device 152 could be used to select which light source is powered, for instance input device 152 could comprise a first button for selecting the first lighting element and a second button for selecting the second lighting element. Input device 153 could be a main power switch utilized to manually turn the master control unit 33 (and light unit 93) on/off. Input device 154 could be used to manually control the luminous intensity (brightness) of the light source(s) which is/are emitting light.

The printed circuit board 150 further comprising circuitry for enabling the rechargeable battery 155 to be recharged, including but not limited to the power jack 34 and the recharger contacts 156. Alternatively, the supply of power through the power jack 34 could be utilized to power the system 13 independent of any power source. The power jack 34 configured for receiving a plug from a recharging transformer. The recharger contacts 156 configured for contacting mating contacts in a charger unit (not illustrated).

The master control unit 33, preferably the printed circuit board 150, further comprises wireless circuitry enabling the master control unit 33 to receive input from the remote control unit 63, as described above with respect to master control system 202 (e.g., UHF, RF, IR, Bluetooth®).

Figure 14:
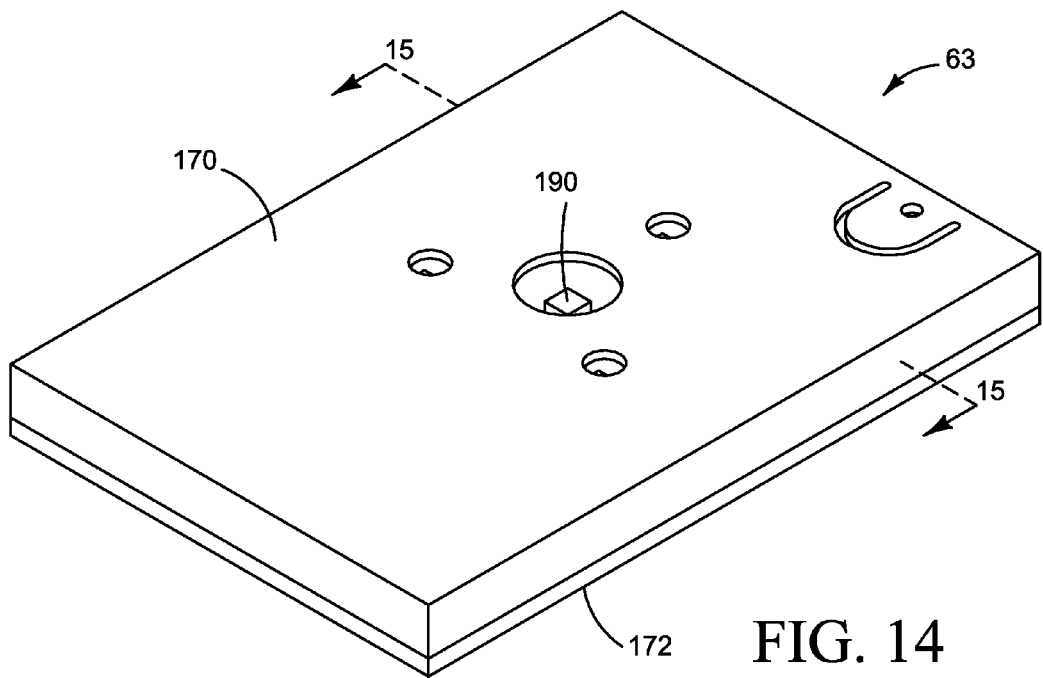
FIG. 14 is a perspective view of the remote control unit of the fourth exemplary hands-free lighting system illustrated in FIG. 2.
Figure 15:
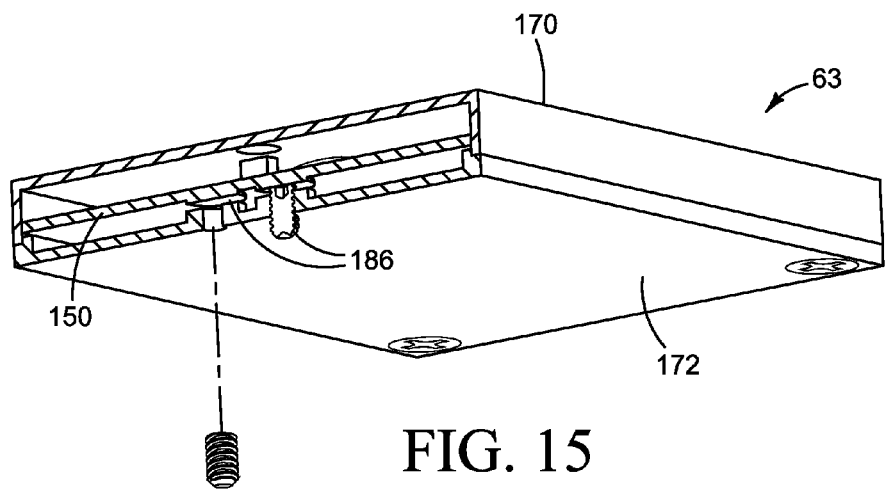
FIG. 15 is a cross-sectional, perspective view along the line 15-15 of FIG. 14.
Figure 16:
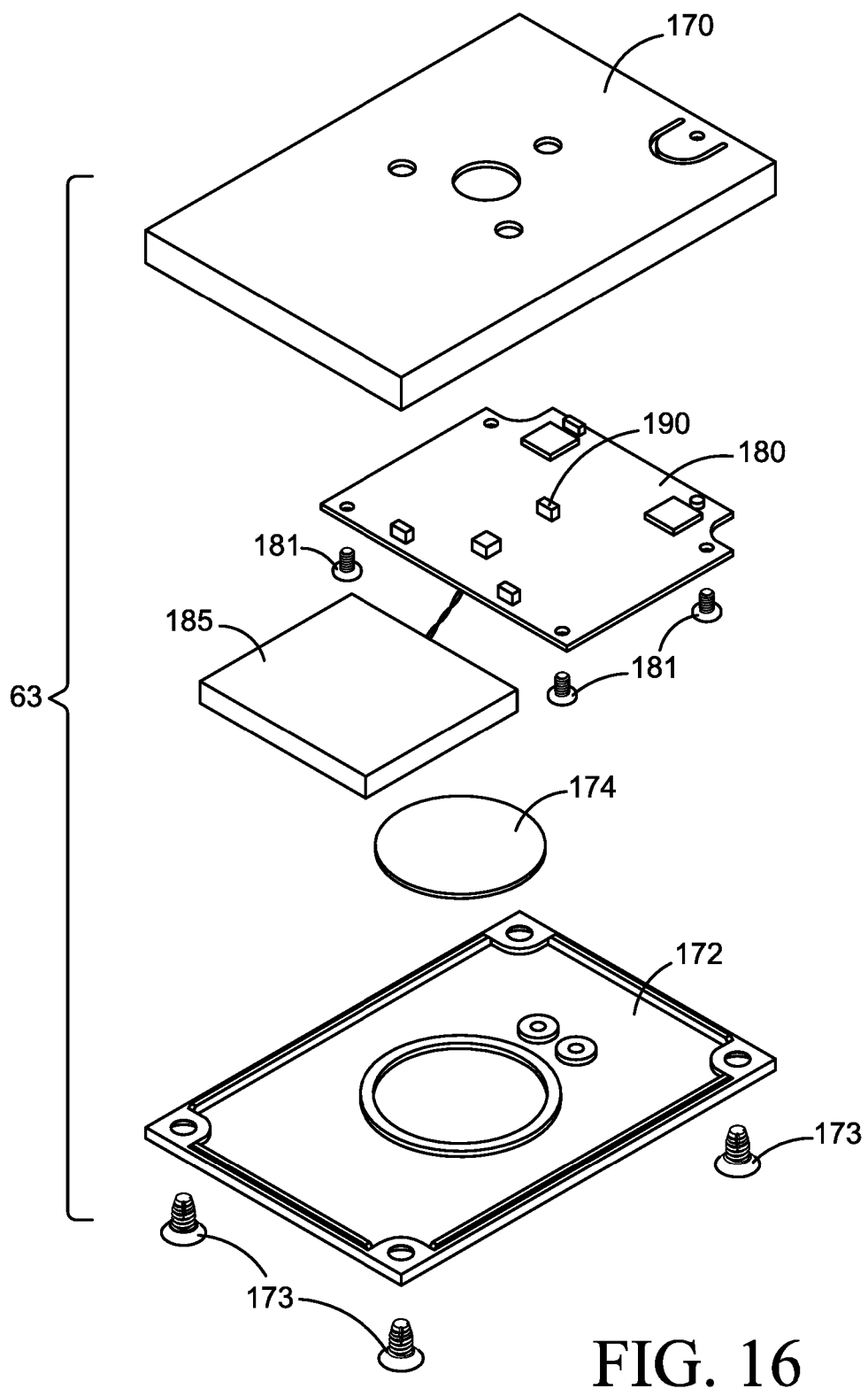
FIG. 16 is an exploded view of the master control unit of FIG. 14.

FIGS. 14, 15 and 16 further illustrate the remote control unit 63 of the fourth exemplary hands-free lighting system 13 illustrated in FIG. 2.

The remote control unit 63 can connect wirelessly, as described above with respect to master control system 202 (e.g., UHF, RF, IR, Bluetooth®), to the master control unit. The remote control unit 63 can signal the master control unit to turn light on/off. The remote control unit 63 can signal the master control unit to turn light brightness up/down.

The remote control unit 63 having a top case 170 and a bottom case 172 which are attached together via a plurality of fasteners 173 to form a housing. The remote control unit 63 comprising a power source 185, such as a rechargeable battery. A magnet 174 may be provided within the housing for enabling the remote control unit 63 to be affixed to a ferromagnetic object, including, but not limited to a work surface, a clip, and a clothing attachment.

The remote control unit 63 comprises a printed circuit board 180 containing the electrical components necessary to operate the remote control unit 63, such as described herein. The printed circuit board 180 further comprises at least one input device for enabling a user to operate the remote control unit 63, for instance a power button for turning the remote control unit 63 on. The printed circuit board 180 further comprising circuitry for enabling the power source 185 to be recharged, including but not limited to recharger contacts 186. The recharger contacts 186 configured for contacting mating contacts in a charger unit (not illustrated). Fasteners 181 may be utilized to fix the printed circuit board 180 in place within the housing, for instance by mounting the printed circuit board 180 to top case 170.

The remote control unit 63 further comprises a sensor 190. The sensor 190, in conjunction with the remote control unit 63, providing a user with the "hands-free" ability to control the operation of the master control unit 33 and/or light unit 93 in the system 13 without necessarily needing to physically touch the master control unit 33, and/or the light unit 93. A skilled artisan will be able to select an appropriate structure and configuration for the sensor in a particular embodiment based on various considerations, including the intended use of the system, the intended arena within which the system will be used, and the equipment and/or accessories with which the system is intended to be used, among other considerations.

A first exemplary sensor comprises a proximity sensor which detects the presence of nearby objects without any physical contact. Utilizing a proximity sensor, a user could make hand (or other bodily) gestures adjacent the sensor to effectuate control of the system and to change settings. For instance, a user swiping his/her hand over the sensor a first time could turn the light unit on, and a second time could turn the light unit off; a user holding his/her hand over the sensor for a predetermined period of time (e.g., three (3) seconds) could trigger the light unit to switch between light elements illuminated; and a user holding his/her hand over the sensor and then moving his/her hand vertically away from the sensor could cause an increase the luminal intensity of the light element, whereas moving his/her hand vertically towards the sensor could cause a decrease in the luminal intensity of the light element.

A second exemplary sensor comprises a capacitive (touch) sensor, for instance a touch screen wherein a user could touch a screen or other surface to operate the system.

A third exemplary sensor comprises a microphone or other acoustic-to-electric transducer. In such a sensor, the microphone could be utilized (with the appropriate sound detection circuitry/software) to allow for voice control of the system, for instance, allowing a user to change the luminous intensity of the light via an audio command.

A fourth exemplary sensor comprises a RFID (radio-frequency identification) sensor for detecting the presence of one or more RFID chips. Such chip(s) could be worn as a separate component (e.g., a bracelet on the wrist). Upon detection of the RFID chip by the RFID sensor, the system could, for instance, turn the light unit on/off.

A fifth exemplary sensor comprises an infrared sensor which detects the presence of an object (e.g., a user's hand) without any physical contact. Utilizing an infrared sensor, a user could make hand (or other bodily) gestures adjacent the sensor to effectuate control of the system and to change settings. For instance, a user swiping his/her hand over the sensor a first time could turn the light unit on, and a second time could turn the light unit off; a user holding his/her hand over the sensor for a predetermined period of time (e.g., three (3) seconds) could trigger the light unit to switch between light elements illuminated; and a user holding his/her hand over the sensor and then moving his/her hand vertically away from the sensor could cause an increase the luminal intensity of the light element, whereas moving his/her hand vertically towards the sensor could cause a decrease in the luminal intensity of the light element.

A sixth exemplary sensor comprises an accelerometer measuring proper acceleration. For instance, an accelerometer could be integrated into the light unit for detecting head motions of a user intended to effectuate control of the system (e.g., nodding head three times to turn light off).

A seventh exemplary sensor comprises a gyroscopic sensor for measuring orientation based on the principles of angular momentum. For instance, in one exemplary gyroscopic sensor, the gyroscopic sensor could be integrated into the light unit for detecting head motions of a user intended to effectuate control of the system (e.g., nodding head three times to turn light off). Such a gyroscopic sensor could read input data to automatically turn light off depending on angle of directed beam—if user looks above or below a certain horizon level the light can be programmed to automatically turn off or back on. In a second exemplary gyroscopic sensor, the gyroscopic sensor could comprise a wrist band worn by the user, the gyroscopic sensor for reading the user's arm and/or wrist movements of a user intended to effectuate control of the system (e.g., shaking arm side to side three times to turn light off).

A seventh exemplary sensor comprises a combination gyroscopic sensor and accelerometer.

Other exemplary sensors include, but are not limited to: foot switches and buttons.

The remote control unit 63, preferably the printed circuit board 180, further comprises wireless circuitry enabling the remote control unit 63 to transmit input data to the master control unit 33, as described above with respect to master control system 202 (e.g., UHF, RF, IR, Bluetooth®).

A ninth exemplary hands-free lighting system comprises a light unit, a master control unit, and a remote control unit. The light unit can be mounted on an accessory, such as a pair of dental loupes (glasses). The master control unit: (1) operates the light, turning it on and off; (2) has buttons for operating the light; (3) has a rechargeable battery; (4) powers the LED light; and (5) connects to the remote control unit. The remote control unit has a sensor that allows a user to operate the light without touching the master control unit. Exemplary sensors include, but are not limited to: a proximity sensor enabling a user to position his/her hand above the sensor; a capacitive sensory; a foot switch; a button; sound/voice control; RFID; infrared; accelerometer; gyroscope. The remote control unit (1) connects wirelessly (e.g., UHF, RF, IR, Bluetooth®) to the master control unit; (2) can signal the master control unit to turn light on/off; and (3) can signal the master control unit to turn light brightness up/down.

A tenth exemplary hands-free lighting system comprises a master control unit (MCU) with a battery pack, a light unit, and a control sensor for operating the light unit (e.g., turning the light unit on and off, adjusting the brightness of the light emitted by the light unit). In the tenth exemplary hands-free lighting system, the master control unit comprises a main circuit board, a power source (e.g., a battery, a rechargeable battery), wireless circuitry, power charging port for allowing a rechargeable battery to be recharged (optional), and power output to deliver power to the light unit. In the tenth exemplary hands-free lighting system, the remote control unit comprises at least one sensor for receiving input from a user, wireless circuitry to transmit input data to the MCU, and a power source (e.g., a battery, a rechargeable battery) for powering the sensor(s). The sensor preferably comprising a proximity sensor to receive hand gesture input from the user to operate the light (e.g., hand gesture input for turning the light on and off, hand gesture input for adjusting the brightness of the light). In the tenth exemplary hands-free lighting system, the light comprises a light emitting diode (LED) light, preferably comprising optics to direct light to a tight spot beam, a heat sink to dissipate heat, a wire to deliver power from a power source to the light, and an attachment apparatus for allowing the light to be attached to an attachment (e.g., a pair of dental loupes).

In an eleventh exemplary hands-free lighting system, the system is similar to the tenth exemplary hands-free lighting system, but the sensor comprises, or also includes, a sound or voice controlled module for receiving sound or voice control input from the user, for instance a remote sensor device with sound detection circuitry to allow voice control for controlling the light unit (e.g., turning light on and off, changing brightness).

In a twelfth exemplary hands-free lighting system, the system is similar to the tenth exemplary hands-free lighting system, but the sensor comprises, or also includes, a RFID (radio-frequency identification) reader for reading a RFID chip worn as a separate component (e.g., a bracelet worn on the user's wrist) that would permit a user to control the light unit (e.g., turning light on and off, changing brightness).

In a thirteenth exemplary hands-free lighting system, the system is similar to the tenth exemplary hands-free lighting system, but the sensor comprises, or also includes, an infrared sensor. The infrared sensor could detect a user's hand motion for controlling the light unit (e.g., turning light on and off, changing brightness).

In a fourteenth exemplary hands-free lighting system, the system is similar to the tenth exemplary hands-free lighting system, but the sensor comprises, or also includes, an accelerometer. The accelerometer could be placed with the light unit, or otherwise worn by the user, for detecting motions that would allow control of the light unit (e.g., turning light on and off, changing brightness).

In a fifteenth exemplary hands-free lighting system, the system is similar to the tenth exemplary hands-free lighting system, but the sensor comprises, or also includes, a gyroscope. The gyroscope could be placed with the light unit, or otherwise located, for detecting user motions that would allow control of the light unit (e.g., turning light on and off, changing brightness).

In a sixteenth exemplary hands-free lighting system, the system is similar to the tenth exemplary hands-free lighting system, but the sensor comprises, or also includes, a gyroscope and an accelerometer. The gyroscope and accelerometer could be utilized together for a more precise sensing of motion for controlling the light unit (e.g., turning light on and off, changing brightness).

In a seventeenth exemplary hands-free lighting system, the remote control unit is worn by the user.

In an eighteenth exemplary hands-free lighting system, the remote control unit is placed on or attached to a surface adjacent the user.

In a nineteenth exemplary hands-free lighting system, the master control unit further comprises recharging dock contacts for allowing the master control unit to be placed into a battery charger unit for charging the master control unit's battery pack.

In a twentieth exemplary hands-free lighting system, the remote control unit further comprises at least one magnet for recharging dock contacts for allowing the master control unit to be placed into a battery charger unit for charging the master control unit's battery pack.

In a twenty-first exemplary hands-free lighting system, the system comprises a master control unit, a light unit, and a remote control unit. The master control unit is configured for controlling the operation of the light unit. The master control unit connects to the light unit, and to the remote control unit. The light unit comprises at least one light source. The light unit is remote from the master control unit. The remote control unit comprises at least one user control for receiving input from a user. Wherein in response to user input, the remote control unit sends a signal to the master control unit. Wherein the master control unit, upon receiving the signal, controls the light unit as instructed by the signal. Preferably, the user control can comprise one or more of an input device, and a sensor. Preferably, the at least one sensor is located external to the remote control unit. Preferably, the master control unit comprises a power source, and preferably the master control unit connects to the light unit via a wired connection, and preferably the power source powers the light unit. Preferably, the master control unit connects to the light unit via a wired connection, and the master control unit controls the light unit via at least one control signal sent through the wired connection. Preferably, the master control unit connects to the remote control unit via a wireless connection, or via a wired connection. Preferably, the master control unit comprises at least one master input device for allowing a user to operate the master control unit. Preferably, the remote control unit comprises a power source.

In a twenty-second exemplary hands-free lighting system, the system comprises a master control unit, a light unit, and a remote control unit. The master control unit is configured for controlling the operation of the light unit. The master control unit connects to the light unit, and to the remote control unit. The master control unit comprises a power source. The master control unit connects to the light unit via a wired connection, and the power source powers the light unit. The light unit comprises at least one light source. The light unit is remote from the master control unit. The remote control unit comprises at least one user control for receiving input from a user. Wherein in response to user input, the remote control unit sends a signal to the master control unit, and the master control unit, upon receiving the signal, controls the light unit as instructed by the signal. Preferably, the user control comprises at least one input device or at least one sensor. Preferably, the master control unit controls the light unit via at least one control signal sent through the wired connection. Preferably, the master control unit connects to the remote control unit via a wireless connection, or via a wired connection. Preferably, the remote control unit comprises a power source.

In a twenty-third exemplary hands-free lighting system, the system comprises a master control unit, a light unit, and a remote control unit. The master control unit is configured for controlling the operation of the light unit. The master control unit connects to the light unit, and to the remote control unit. The master control unit comprises a power source. The master control unit connects to the light unit via a wired connection. The power source powers the light unit. The light unit comprises at least one light source. The light unit is remote from the master control unit. The remote control unit comprises at least one user control for receiving input from a user. The user control comprises at least one sensor. Wherein in response to user input, the remote control unit sends a signal to the master control unit, and wherein the master control unit, upon receiving the signal, controls the light unit as instructed by the signal. Preferably, the master control unit controls the light unit via at least one control signal sent through the wired connection, and the master control unit connects to the remote control unit via a wireless connection.

In a first exemplary light unit system, the light unit system comprises a first light source, a second light source, a master control unit, and a power source. The first light source comprising at least one first light element configured as a dental curing light. The second light source comprising at least one second light element configured as an illuminating light. The master control unit configured for controlling the operation of the first and second light sources. The power source for supplying power to the first and/or second light sources. Preferably, the first light element comprises a light emitting diode. Preferably, second light element comprises a light emitting diode. Preferably, the power source is a battery. Preferably, the first light element and the second light element emit light in the visible blue light spectrum, and the second light source further comprises a visible blue light spectrum filter for preventing the passing of visible blue light from the second light element through the filter.

In a second exemplary light unit system, the light unit system comprises a first light source, a second light source, a master control unit, and a power source. The first light source comprising at least one first light element configured as a dental curing light. The second light source comprising at least one second light element configured as an illuminating light. The master control unit configured for controlling the operation of the first and second light sources. The power source for supplying power to the first and/or second light sources. Preferably, the first light element comprises a light emitting diode. Preferably, second light element comprises a light emitting diode. Preferably, the power source is a battery. Preferably, the first light element emits light in the visible blue light spectrum, and said second light element does not emit light in the visible blue light spectrum. Preferably, the second light element comprises a light emitting diode emitting light in the visible blue light spectrum, and the light emitting diode is a light emitting diode using gallium nitride as a semiconductor.

Any suitable structure and/or material can be used for the components of the lighting system, and a skilled artisan will be able to select an appropriate structure and material for the components in a particular embodiment based on various considerations, including the intended use of the lighting system, the intended arena within which the lighting system will be used, and the equipment and/or accessories with which the lighting system is intended to be used, among other considerations.

It is noted that all structure and features of the various described and illustrated embodiments can be combined in any suitable configuration for inclusion in a lighting system according to a particular embodiment. For example, a lighting system according a particular embodiment can include neither, one, or both of proximity sensor and the RFID reader described above.

The foregoing detailed description provides exemplary embodiments of the invention and includes the best mode for practicing the invention. The description and illustration of these embodiments is intended only to provide examples of the invention, and not to limit the scope of the invention, or its protection, in any manner.

What is claimed is:

1. A hands-free lighting system, said hands-free lighting system comprising:
   a master control unit, a light unit, and a remote control unit;
   wherein said master control unit is configured for controlling the operation of said light unit, said master control unit connects to said light unit, said master control unit connects to said remote control unit;
   wherein said light unit comprises at least one light source, wherein said light unit is remote from said master control unit;
   wherein said remote control unit comprises at least one user control for receiving input from a user, wherein said user control comprises at least one input device; and
   wherein in response to user input, said remote control unit sends a signal to the master control unit, wherein said master control unit, upon receiving said signal, controls the light unit as instructed by the signal.

2. The hands-free lighting system of claim 1, wherein said input device receives a command selection via voice recognition.

3. The hands-free lighting system of claim 1, wherein said user control comprises a proximity sensor.

4. The hands-free lighting system of claim 1, wherein said user control comprises a microphone.

5. The hands-free lighting system of claim 1, wherein said user control comprises a acoustic-to-electric transducer.

6. The hands-free lighting system of claim 1, wherein said user control comprises a radio-frequency identification (RFID) sensor.

7. The hands-free lighting system of claim 1, wherein said user control comprises a infrared sensor.

8. The hands-free lighting system of claim 1, wherein said user control comprises an accelerometer.

9. The hands-free lighting system of claim 1, wherein said user control comprises a gyroscopic sensor.

10. The hands-free lighting system of claim 1, further comprising a power source, and wherein said at least one light source comprises a first light source and a second light source, wherein said first light source comprises at least one first light element configured as a dental curing light, and wherein said second light source comprises at least one second light element configured as an illuminating light, wherein said first light element comprises a light emitting diode, and wherein said second light element comprises a light emitting diode, wherein the light emitting diode of the second light element is a light emitting diode using gallium nitride as a semiconductor.

11. The hands-free lighting system of claim 1, further comprising a power source, wherein said power source is a battery, and wherein said at least one light source comprises a first light source and a second light source, wherein said first light source comprises at least one first light element configured as a dental curing light, and wherein said second light source comprises at least one second light element configured as an illuminating light.

\* \* \* \* \*